United States Patent
Huynh et al.

(10) Patent No.: US 7,119,179 B1
(45) Date of Patent: Oct. 10, 2006

(54) PREPARATION OF HIGH NITROGEN COMPOUND AND MATERIALS THEREFROM

(75) Inventors: My Hang V. Huynh, Los Alamos, NM (US); Michael A. Hiskey, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/085,395

(22) Filed: Mar. 21, 2005

(51) Int. Cl.
*C07D 403/12* (2006.01)
*C01C 3/00* (2006.01)

(52) U.S. Cl. .................. 534/767; 544/198; 423/364; 423/384

(58) Field of Classification Search ................ 534/767; 544/198; 423/364, 384
See application file for complete search history.

(56) References Cited

U.S. PATENT DOCUMENTS 5,840,435 A * 11/1998 Lieber et al. ............... 428/698
5,981,094 A * 11/1999 Teter et al. ................. 428/698
6,428,762 B1 * 8/2002 Khabashesku et al. ...... 423/384

OTHER PUBLICATIONS

Huynh et al., Angew. Chem. Int. Ed., 44(5), 737-739, Jan. 21, 2005.*
Gillan, Synthesis of Nitrogen-Rich Carbon Nitride Networks from an Energetic Molecular Azide Precursor, Chem. Mater., vol. 12 (2000) pp. 3906-3912.
Wilson, "Old Molecules, New Chemistry," Science & Technology, vol. 82 (2004) pp. 34-35.
Kroke et al., "Novel Group 14 Nitrides," Coordination Chemistry Reviews 248, (2004) pp. 493-532.
Miller et al., "Rapid, Facile Synthesis of Nitrogen-Rich Carbon Nitride Powders," J. Mater. Chem, vol. 12, (2002) pp. 2463-2469.
Wang et al., "Deposition of Carbon Nitride Films From Single-Source s-triazine Precursors," Carbon, vol. 41 (2003) pp. 2031-2037.
Komatsu, "Prototype Carbon Nitrides Similar to the Symmetric Triangular Form of Melon," J. Mater. Chem., vol. 11 (2001) pp. 802-805.
Kroke et al., "Tri-s-triazine Derivatives. Part I. From Trichloro-tri-s-triazine to Graphitic $C_3N_4$ Structures," New J. Chem., vol. 26 (2002) pp. 508-512.
Jürgens, et al., "Melem (2,5,8-Triamino-tri-s-triazine), an Important Intermediate During Condensation of Melamine Rings to Graphitic Carbon Nitride: Synthesis, Structure Determination by X-Ray Powder Diffractometry, Solid-State NMR, and Theoretical Studies," J. Am. Chem. Soc., vol. 125 (2003) pp. 10288-10300.
Loew et al., "Azo-1,3,5-Triazines" J. Heterocyclic Chem.,, vol. 13 (1976), pp. 829-833.
Huynh et al., "Polyazido High-Nitrogen Compounds: Hydrazo- and Azo-1,3,5-Triazine," Angew. Chem. Int. Ed., vol. 43 (2004) pp. 4924-4928.
Huynh et al., "3.6-Di(azido)-1,2,4,5-Tetrazine: A Precursor for the Preparation of Carbon Nanospheres and Nitrogen-Rich Carbon Nitrides," Angew. Chem. Int. Ed., vol. 43 (2004) pp. 5658-5661.
Ritter, "Chock Full of Nitrogen," Science & Technology, vol. 82 (2004) p. 44.
Widlow et al, "Recent Progress in the Synthesis and Characterization of Amorphous and Crystalline Carbon Nitride Coatings," Brazilian Journal of Physics, vol. 30 (2000) pp. 490-498.
Cui et al., "A Review of Investigations on Biocompatibility of Diamond-Like Carbon and Carbon Nitride Films," Surface and Coatings Technology, vol. 131 (2000) pp. 481-487.

* cited by examiner

*Primary Examiner*—Fiona T. Powers
(74) *Attorney, Agent, or Firm*—Samuel L. Borkowsky

(57) ABSTRACT

The high-nitrogen compound of the formula

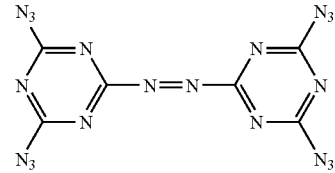

was prepared. Pyrolysis of the compound yields carbon nitrides $C_2N_3$ and $C_3N_5$. The carbon nitrides vary in their density, texture, and morphology.

4 Claims, 3 Drawing Sheets

PREPARATION OF HIGH NITROGEN COMPOUND AND MATERIALS THEREFROM

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to high-nitrogen compounds and more particularly to the preparation of the high-nitrogen compound 4,4',6,6'-tetra(azido)azo-1,3,5-triazine (TAAT), and carbon nitrides from the high-nitrogen compound.

BACKGROUND OF THE INVENTION

Carbon nitrides have interesting mechanical, optical, and tribological properties. These super-hard diamond-like materials have low densities, are extremely wear resistant, and are generally chemically inert. Carbon nitrides are used in biocompatible coatings for medical implants, battery electrodes, gas separation systems, corrosive protection, humidity and gas sensors, and other applications. The applications for carbon nitrides generally depend on particle size and texture and on the relative nitrogen content of the carbon nitride.

An extensive effort has been focused on the synthesis of precursors and the development of methods to control the size, regulate the texture, and increase the nitrogen content in carbon nitrides.

There have been recent reports describing the use of energetic "high-nitrogen" compounds for preparing carbon nitrides. High-nitrogen compounds are a relatively new class of energetic compounds whose energy is largely derived from their very high positive heats of formation that result from the large number of energetic N—N and C—N bonds in these compounds. SCHEME 1 shows the formulas of three high-nitrogen compounds (DAAT: 3,3'-azobis(6-amino-1,2,4,5-tetrazine); BTATz: 3,6-bis-(1H-1,2,3,4-tetrazol-5-ylamino)-1,2,4,5-tetrazine; and TAG-AT: triaminoguanidinium 5,5'-azobis(1H-tetrazolate)) and their associated heats of formation.

SCHEME 1

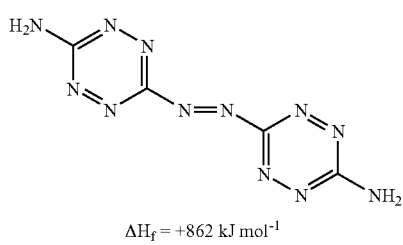

DAAT $\Delta H_f = +862$ kJ mol$^{-1}$

-continued

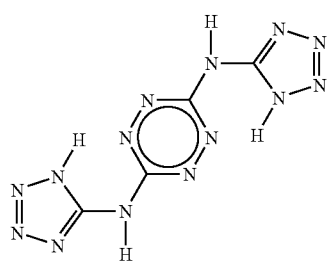

BTATz $\Delta H_f = +883$ kJ mol$^{-1}$

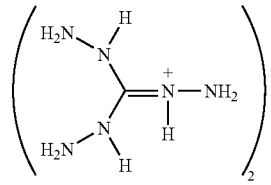

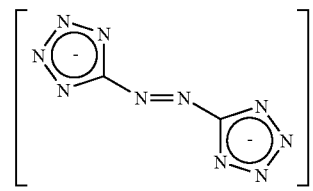

TAG-AT $\Delta H_f = +1075$ kJ mol$^{-1}$

High-nitrogen compounds that contain polyazido groups possess even higher heats of formation. In general, however, compounds with polyazido groups are extremely sensitive to spark, friction, and impact (H$_{50}$) and generally exhibit poor thermal stability. Therefore, applications for these types of compounds tend to be limited. Gillan, however, has reported the preparation of carbon nitrides C$_3$N$_4$ and C$_3$N$_5$ from 2,4,6-tri(azido)-1,3,5-triazine [1]. The formulas of 2,4,6-tri(azido)-1,3,5-triazine and another high-nitrogen compound having polyazido groups are shown in SCHEME 2 below, along with some data related to their melting points, decomposition temperatures, heats of formation, and sensitivities to spark, friction, and impact.

SCHEME 2.

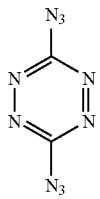

3, 6-Di(azido)- 1, 2, 4, 5 - tetrazine
MP = Not Observable
DSC Exo. = 130° C. dec.
$H_{50} < 1$ cm
Friction < 0.5 kg
Spark < 0.36 J
$\Delta H_f(Ext.) = +1101$ kJ mol$^{-1}$

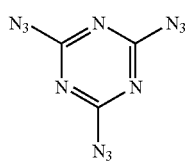

2, 4, 6-Tri(azido)- 1, 3, 5 - triazine
MP = 94° C.
DSC Exo. = 187° C. dec.
$H_{50} = 6.2$ cm
Friction < 0.5 kg
Spark < 0.36 J
$\Delta H_f = +1035$ kJ mol$^{-1}$ Other reported preparations of carbon nitrides using other types of precursors generally involve applied pressure, high temperature and/or shock compression, and the products obtained are often nitrogen poor materials that are occasionally contaminated with hydrogen-containing by-products [2–8].

High-nitrogen compounds with better thermal stability and less sensitivity to spark, friction, and/or impact than known precursors would be better precursor materials for carbon nitrides.

There remains a need for better precursor materials for carbon nitrides.

Accordingly, an object of the present invention is to provide better high-nitrogen compound precursor materials for preparing carbon nitrides.

Another object of the present invention is to provide a method for preparing carbon nitrides from high-nitrogen compounds.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a chemical compound of the formula

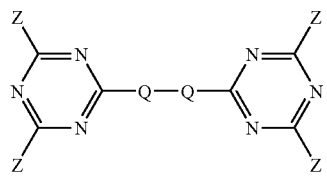

wherein Z is selected from —$N_3$ and —$NHNH_2$; and wherein —Q—Q— is selected from —NH—NH— and —N=N—.

The invention also includes a method for preparing carbon nitrides that involves heating a compound of the formula

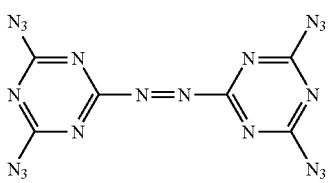

to a temperature sufficiently high to melt but not substantially decompose the compound, and then heating the melted compound to a temperature sufficiently high to decompose the compound and form carbon nitrides.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION

Figure 1:
FIG. 1 shows a scanning electron microscope (SEM) image of the carbon nitride $C_2N_3$ prepared according to the invention.

This invention is concerned with the preparation high-nitrogen compounds and with the preparation of carbon nitrides from high-nitrogen compounds. The invention is particularly concerned with the preparation of the high nitrogen compound 4,4',6,6'-tetra(azido)hydrazo-1,3,5-triazine and the conversion of this compound to 4,4',6,6'-tetra(azido)azo-1,3,5-triazine (TAAT), and also with the conversion of TAAT to carbon nitrides.

An exemplary sequence of chemical reactions used for synthesizing TAAT is shown in SCHEME 3 below.

SCHEME 3.

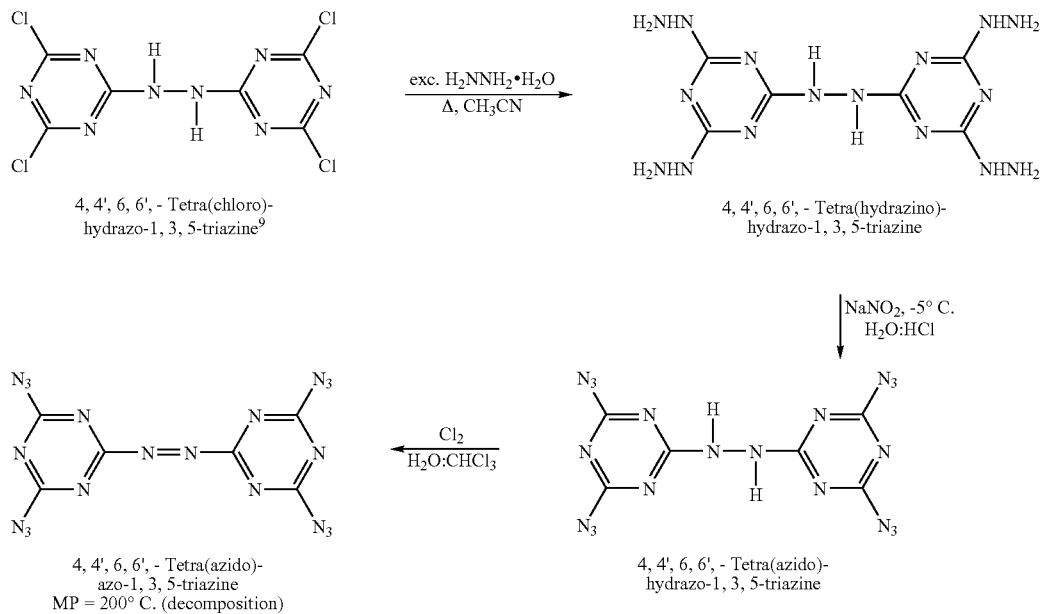

Briefly, 4,4',6,6'-tetra(chloro)hydrazo-1,3,5-triazine (1) [9] reacts rapidly with an excess of hydrazine monohydrate in acetonitrile to give 4,4',6,6'-tetra(hydrazino)-hydrazo-1,3,5-triazine (2). Compound (2) undergoes diazotization to yield 4,4',6,6'-tetra(azido)hydrazo-1,3,5-triazine (3). A suspension of (3) in 1:2 (v/v) $H_2O:CHCl_3$ solution reacts with chlorine gas at room temperature to provide 4,4',6,6'-tetra(azido)azo-1,3,5-triazine (4, TAAT).

Compounds (2), (3), and (4) were all isolated and characterized by elemental analysis, Differential Scanning Calorimetry (DSC), heat of formation, and infrared and $^1H/^{13}C$ NMR spectroscopy. The structures of compounds (3) and (4) were also characterized by x-ray crystallography.

The explosive properties and sensitivity of 4,4',6,6'-tetra(azido)hydrazo-1,3,5-triazine (3) and 4,4',6,6'-tetra(azido)azo-1,3,5-triazine (4, TAAT) were determined. TABLE 1 below provides a comparison of the decomposition temperature, impact, friction, and spark sensitivities of (3) and (4) with 2,4,6-triazido-1,3,5-triazine and also with the well-known explosive pentaerythritol tetranitrate (PETN).

TABLE 1

Explosive Properties and Sensitivity

| Compound | DSC Fast Decomposition (° C.) | Impact sensitivity (Type 12) (cm) | Friction sensitivity (BAM) (Kg) | Spark sensitivity (J) |
|---|---|---|---|---|
| PETN | 178 | 14.5 | 5.4 | >0.36 |
| 2,4,6-triazido-1,3,5-triazine | 187 | 6.2 | <0.5 | <0.36 |
| Tetra(azido)hydrazo-1,3,5-triazine (3) | 202 | 18.3 | 2.9 | <0.36 |
| Tetra(azido)azo-1,3,5-triazine (4) (TAAT) | 185 | 6.2 | 2.4 | <0.36 |

As TABLE 1 indicates, 2,4,6-triazido-1,3,5-triazine is extremely sensitive to friction and spark, and its impact sensitivity is much greater than that of PETN. Tetra(azido)hydrazo-1,3,5-triazine (3) is about as spark sensitive as 2,4,6-triazido-1,3,5-triazine, but is much less impact and friction sensitive. Tetra(azido)azo-1,3,5-triazine (TAAT, 4) is comparable to 2,4,6-triazido-1,3,5-triazine in impact and spark sensitivity, but is much less sensitive to friction.

It is believed that the hydrazo and azo linkages in tetra(azido)hydrazo-1,3,5-triazine (3) and TAAT (4) desensitize these compounds and decrease their volatility, which results in a non-observable melting point up to their fast decomposition at 185 and 202 degrees Celsius (measured using Differential Scanning Calorimetry, DSC), respectively.

The present invention is more particularly described in the following EXAMPLES. Each procedure was carried out at an initial atmospheric pressure of about 580 torr (11.2 psi or 0.76 atm) and a relative humidity of less than about 15 percent. The temperatures were maintained to within +2 degrees Celsius. Each EXAMPLE describing the preparation of carbon nitride was performed three times.

EXAMPLE 1

Synthesis of 4,4',6,6'-tetra(chloro)hydrazo-1,3,5-triazine (1). 4,4',6,6'-tetra(chloro)hydrazo-1,3,5-triazine (1) was synthesized as described by P. Loew and C. D. Weis in Journal of Heterocyclic Chemistry 1976, 13, pp. 829–833, hereby incorporated by reference. The crude product was extracted with acetonitrile for 2 hours and filtered to remove an insoluble by-product. The acetonitrile was removed by rotary evaporation at room temperature, and the dried product was stored in the freezer to avoid its further decomposition. $^1H$ NMR (DMSO-$d_6$) δ 10.59 (s, 2H); $^{13}C$ NMR (DMSO-$d_6$) δ 168.31, 169.58, 170.28.

EXAMPLE 2

Synthesis of 4,4', 6,6'-tetra(hydrazino)-hydrazo-1,3,5-triazine (2). A solution of 4,4',6,6'-tetra(chloro)hydrazo-1,3,5-triazine (3.28 g, 10 millimoles) (1) in acetonitrile (200 ml) was prepared and cooled to 0 degrees Celsius. A solution of hydrazine (1.93 g, 60.2 mmol) in acetonitrile (10 ml) was also prepared. The hydrazine solution was added to the cold solution of compound (1) with vigorous overhead stirring. After the addition, the resulting mixture was refluxed for 2 hrs, then cooled to room temperature. The mixture was filtered, and the damp filter cake was washed thoroughly with water and air dried to yield 3.02 g (97%) of 4,4',6,6'-tetra(hydrazino)-hydrazo-1,3,5-triazine (2) as a white solid. Compound (2) decomposes rapidly at a temperature of 293 degrees Celsius, as determined by DSC. Compound (2) was also analyzed by NMR and IR spectroscopy and by elemental analysis. The data are as follows: $^{13}$C NMR (DMSO-d$_6$/DCl/D$_2$O) δ 164.89, 165.36, 167.66. Elemental analysis calculated for $C_6H_{14}N_{16}$: C, 23.23; H, 4.55; N, 72.23; Found: C, 23.47; H, 4.65; N, 70.36. Infrared (cm$^{-1}$): ν(N—H) 3312 (s) and 3269 (s); ν(triazine) 1571 (vs), 1523 (vs), 1073 (vs), 941 (vs), and 801 (vs). ΔH$_f$=+406±5 kJ/mol.

EXAMPLE 3

Synthesis of 4,4',6,6'-tetra(azido)hydrazo-1,3,5-triazine (3). To a jacketed beaker containing 40 ml of 3.5 M HCl was added 4,4',6,6'-tetra(hydrazino)-hydrazo-1,3,5-triazine (0.5 g, 1.61 mmol) (2) and the resulting suspension was stirred until compound (2) completely dissolved. The resulting solution was cooled to a temperature of about –5 degrees Celsius, after which a solution of NaNO$_2$ (1.33 g, 19.27 mmol) in water (10 ml) was added with vigorous stirring while the temperature of the mixture was kept below 3 degrees Celsius. A few drops of ethyl ether were also added in order to control the foaming that occurred during the addition. The pale yellow crude product was re-crystallized from acetonitrile to yield 0.5 g (87%) of 4,4',6,6'-tetra(azido) hydrazo-1,3,5-triazine (3). Compound (3) does not melt, but rather starts to undergo fast decomposition at a temperature of 202 degrees Celsius, as determined by DSC. Compound (3) was also analyzed by NMR and IR spectroscopy and by elemental analysis. The data are as follows: $^1$H NMR (DMSO-d$_6$) δ 10.6 (s, 2H); $^{13}$C NMR (DMSO-d$_6$) δ 168.3, 169.6, 170.2. Elemental analysis calculated for $C_6H_2N_{20}$: C, 20.34; H, 0.57; N, 79.09; Found: C, 20.04; H, 0.75; N, 79.44. Infrared (cm$^{-1}$): ν(N$_3$) 2172 (vs) and 2129 (vs); ν(N—H) 3221 (s) and 3091 (s); ν(triazine) 1541 (vs), 1352 (vs), 1252 (vs), 972 (vs), and 806 (vs). ΔH$_f$=+1753±3 kJ/mol.

The structure of compound (3) was confirmed using X-ray crystallography. Briefly, compound (3) crystallized as one polymorph in which the two 1,3,5-triazine rings are not co-planar but have a central torsion angle of 105°.

EXAMPLE 4

Synthesis of 4,4,6,6'-tetra(azido)azo-1,3,5-triazine (4, TAAT). A solution of sodium hydrogen carbonate (0.475 g, 5.65 mmol) in 15 ml of water was added to a suspension of 4,4',6,6'-tetra(azido)hydrazo-1,3,5-triazine (1.0 g, 2.82 mmol) (3) in ml of chloroform. A slow stream of chlorine gas was bubbled through the chloroform layer with gentle stirring until a dark reddish orange homogeneous chloroform layer was formed. The organic layer was separated and dried with magnesium sulfate. The volume of the solution was reduced to 15 ml and then passed down a silica gel column using chloroform as the eluent. The product 4,4',6,6'-tetra(azido)azo-1,3,5-triazine (4, TAAT) crystallized on standing at room temperature for a few days. Yield: 0.746 g (75%). Compound (4) became viscous at a temperature of 150 degrees Celsius (or when a trace of solvent remained). Compound (4) decomposed at a temperature of 200 degrees Celsius, as determined by DSC. Compound (4) was also analyzed by NMR and IR spectroscopy and by elemental analysis. The data are as follows: $^{13}$C NMR (acetone-d$_6$) δ 173.7, 176.4. Elemental analysis calculated for $C_6N_{20}$: C, 20.46; H, 0.00; N, 79.54; Found: C, 20.82; H, 0.07; N, 79.18. Infrared (cm$^{-1}$): ν(N$_3$) 2208 (vs), 2155 (vs), and 2132 (vs); ν(triazine) 1549 (vs), 1521 (vs), 1435 (vs), 1161 (vs), 1011 (vs), and 823 (vs). ΔH$_f$=+2171±10 kJ/mol.

The azido groups present in compound (4) do not tautomerize to form fused tetrazolo rings, even when compound (4) is heated in a polar solvent.

X-ray crystallography was used to confirm the structure of compound 4, TAAT. Briefly, TAAT crystallizes as α and β polymorphs. The β polymorph has two conformers. The azido substituents of these two conformers are oriented in different directions.

It is believed that the heat of formation for TAAT (ΔH=+2171 kJ/mol) is the highest ever experimentally measured for an energetic high-nitrogen energetic compound.

EXAMPLE 5

Preparation of carbon nitride $C_2N_3$ from TAAT. The nitrogen-rich carbon nitride $C_2N_3$ was prepared under a nitrogen atmosphere as follows. A crystalline sample of TAAT (1.0 gram) was loaded into a 50 ml stainless steel bomb. The bomb was then heated to a temperature of about 160 degrees Celsius over a period of about three hours, and the temperature was maintained for another four hours. The temperature was then increased to about 185 degrees Celsius over a five-hour period. This temperature was maintained overnight. The product recovered from the bomb was glassy, nanolayered $C_2N_3$ carbon nitride. The density of the product was 1.32±0.01 g cm$^{-3}$.

An SEM image of the product is shown in FIG. 1. The interlinked three-dimensional network of glassy pockets suggests that several phase changes occurred during the conversion to $C_2N_3$. While not intending to be bound by any particular explanation, the structure of the product can be explained as follows: when the temperature was raised from room temperature to 160 degrees Celsius, TAAT became viscous, and gradually liquefied as the temperature approached 185 degrees Celsius. At 185 degrees Celsius, the liquid TAAT slowly decomposed, slowly releasing nitrogen gas and forming glassy nanolayered carbon nitride product with an interconnected pocket-like structure. The glassy product was characterized by infrared spectroscopy, Gas Pycnometry (GP), elemental analysis, and Thermogravimetric Analysis (TGA). The data are as follows: Infrared (cm$^{-1}$, Nujol mull): 1456 (vs), 1367 (vs), 1342 (vs), 1303 (vs), 1080 (vs), 848 (s), 804 (vs), and 398 (vs). GP: ρ=1.32±0.01 g cm$^{-3}$. Elemental analysis, found: C, 36.34; H, 0.58; N, 63.07. TGA: The material is robust up to about 670 degrees Celsius.

EXAMPLE 6

Preparation of $C_3N_5$ carbon nitride from TAAT. The nitrogen-rich $C_3N_5$ carbon nitride was prepared as follows: Under a nitrogen atmosphere in a 50 ml stainless steel bomb, crystalline TAAT (1.0 gram) was heated to a temperature of about 160 degrees Celsius for about three hours. The temperature was maintained for another four hours, then increased to about 200 degrees Celsius over a five-hour period, and maintained at 200 degrees Celsius overnight. The recovered product was a low-density (p=0.44±0.01 g cm$^{-3}$) carbon nitride.

Figure 2:
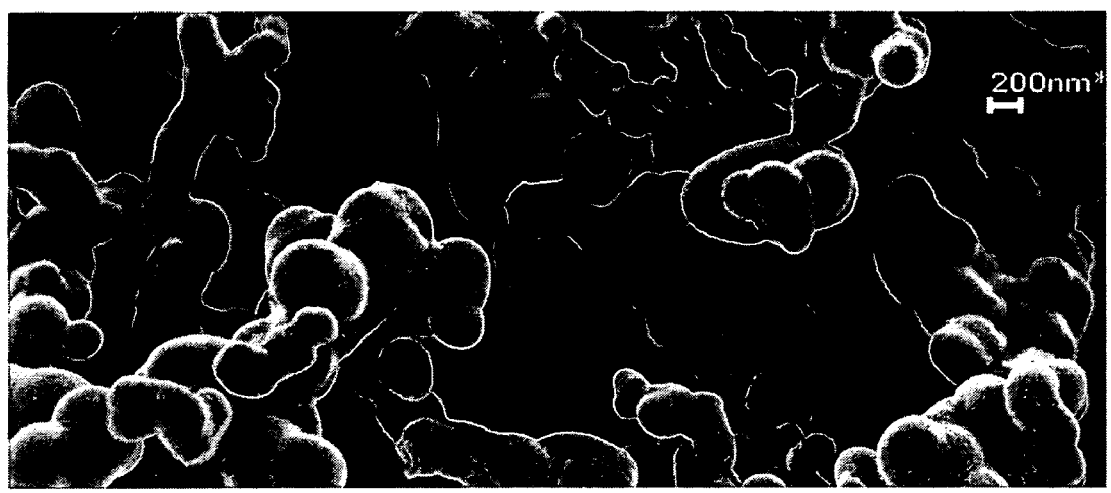
FIG. 2 shows an SEM image of a low-density $C_3N_5$ carbon nitride prepared according to the invention.

An SEM image of the product is shown in FIG. 2. The product appears to have a tunnel-like structure with spherical- and elliptical-shaped nanoclusters.

The product $C_3N_5$ carbon nitride was also characterized by infrared spectroscopy, elemental analysis, and TGA. The data are as follows: Infrared (cm$^{-1}$, Nujol mull): 1641 (vs), 1565 (vs), 1461 (vs), 1307 (vs), 1244 (vs), 968 (s), 814 (vs), and 374 (vs) presumably due to conjugated C=N/C=C portions, aromatic ring modes, aromatic C—N bonds, and C—C bonds. Elemental analysis found: C, 33.18; H, 0.63; N, 65.89. TGA: the material is robust up to about 650 degrees Celsius.

EXAMPLE 7

Second preparation of $C_3N_5$ carbon nitride from TAAT. The crystalline TAAT was heated from room temperature to 205 degrees Celsius over a four-hour period and then maintained at this temperature overnight. During the period of four hours heating from room temperature to 205 degrees Celsius, rapid release of gas ($N_2$) accompanied the conversion of TAAT to carbon nitride.

Figure 3:
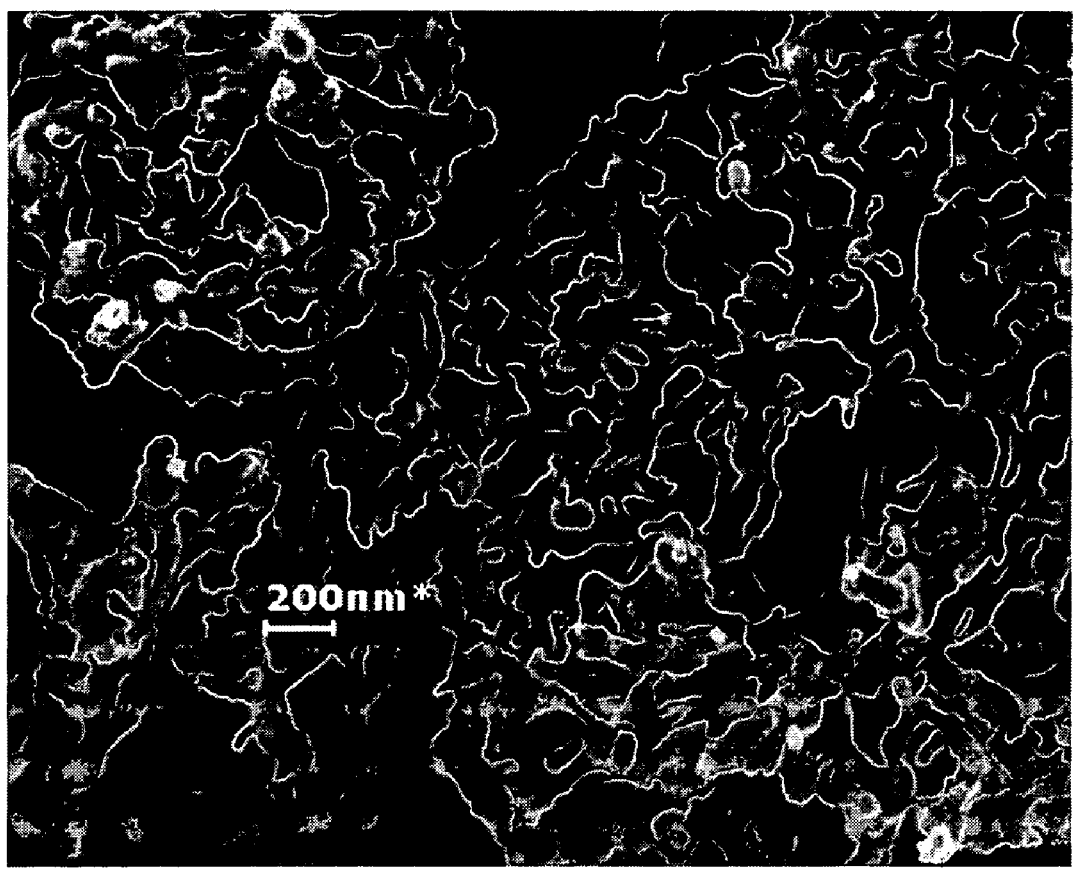
FIG. 3 shows an SEM image of $C_3N_5$ carbon nitride having a nanodendritic morphology and prepared according to the invention.

An SEM image of the product is shown in FIG. 3. This product appears to have a nanodendritic morphology with interlinked segments having diameters in a range from about 10 nanometers (nm) to about 100 nm.

The product particles of $C_3N_5$ carbon nitride were smaller than those of EXAMPLE 5, and also more than twice as dense (p=1.08±0.01 g cm$^{-3}$).

The nanodendritic $C_3N_5$ carbon nitride product was also characterized by elemental analysis, and TGA. The data are as follows: Infrared (cm$^{-1}$, Nujol mull): 1640 (vs), 1564 (vs), 1461 (vs), 1304 (vs), 1246 (vs), 968 (s), 815 (vs), and 378 (vs). Elemental analysis found: C, 33.26; H, 0.29; N, 65.70. TGA: robust up to about 650 degrees Celsius.

In summary, this invention is directed to a simple synthesis of TAAT and to the preparation of carbon nitrides from TAAT. TAAT is an excellent precursor for nitrogen-rich carbon nitrides. The pyrolysis reactions are simple, occur under mild conditions, and products do not require any further purification. The pyrolysis to carbon nitride is thermodynamically favorable and does not generate any hazardous environmental waste.

The foregoing description of the invention has been presented for purposes of illustration and description and is not intended to be exhaustive or to limit the invention to the precise form disclosed, and obviously many modifications and is variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

REFERENCES

The following references are incorporated by reference herein.
1. E. G. Gillan, *Chem. Mater.* 2000, vol. 12, pp. 3906–3912.
2. E. K. Wilson, *Chem. & Eng. News* 2004, vol. 82, pp. 34–35.
3. E. Kroke, M. Schwarz, *Coord. Chem. Rev.* 2004, vol. 248, pp. 493–532.
4. D. R. Miller, J. J. Wang, E. G. Gillan, *J. Mater. Chem.* 2002, vol. 12, pp. 2463–2469.
5. J. J. Wang, D. R. Miller, E. G. Gillan, *Carbon* 2003, vol. 41, pp. 2031–2037.
6. T. Komatsu, *J. Mater. Chem.* 2001, vol. 11, pp. 802–805.
7. E. Kroke, M. Schwarz, E. Horath-Bordon, P. Kroll, B. Noll, A. D. Norman, *New J. Chem.* 2002, vol. 26, pp. 508–512.
8. B. Jurgens, E. Irran, J. Senker, P. Kroll, H. Muller, W. Schnick, *J. Am. Chem. Soc.* 2003, vol. 125, pp. 10288–10300.
9. P. Loew, C. D. Weis, *J. Heterocyclic Chem.* 1976, vol. 13, pp. 829–833.

What is claimed is:

1. An isolated chemical compound of the formula

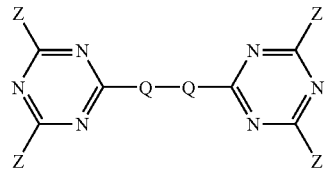

wherein Z is selected from the group consisting of —$N_3$ and —$NHNH_2$; and
wherein —Q—Q— is selected from the group consisting of —NH—NH— and —N=N—.

2. A method for preparing carbon nitride comprising heating a compound of the formula

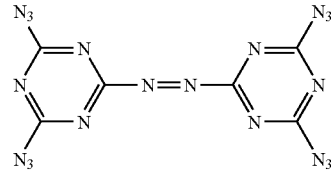

to a temperature sufficiently high to melt but not substantially decompose the compound, and then heating the melted compound to a temperature sufficiently high to decompose the compound and form carbon nitride.

3. The method of claim 2, wherein the carbon nitride comprises $C_2N_3$.

4. The method of claim 2, wherein the carbon nitride comprises $C_3N_5$.

* * * * *